United States Patent [19]

Hawman et al.

[11] Patent Number: 5,070,722
[45] Date of Patent: Dec. 10, 1991

[54] TURBINE ENGINE DEBRIS INGESTION MONITOR

[75] Inventors: Michael W. Hawman, New Britian; Thomas M. Ritter, Wethersfield; Timothy M. Remmers, Winsted, all of Conn.

[73] Assignee: United Technologies Corporation, Hartford, Conn.

[21] Appl. No.: 586,630

[22] Filed: Sep. 21, 1990

[51] Int. Cl.$^5$ .............................. G01N 15/07
[52] U.S. Cl. .................................. 73/28.01
[58] Field of Search ............... 73/23.21, 24.03, 28.01, 73/28.03, 31.04, 116, 170 R; 340/945; 415/118; 364/424.06

[56] References Cited

U.S. PATENT DOCUMENTS

| 2,944,250 | 7/1960 | Dutt | 73/170 R |
|---|---|---|---|
| 3,159,029 | 12/1964 | Ruderman | 73/28.01 |
| 3,245,078 | 4/1966 | Kohl | 73/170 R |
| 3,309,518 | 3/1967 | Weiss | 73/28.01 |
| 3,805,591 | 4/1974 | Willis et al. | 73/24.03 |
| 3,952,586 | 4/1976 | Hanson et al. | 73/116 |
| 3,993,017 | 11/1976 | Debrey | 73/28.01 |
| 4,055,089 | 10/1977 | Shriver | 73/23.01 |
| 4,135,246 | 1/1979 | McMannis | 73/116 |
| 4,296,628 | 10/1981 | Mast | 73/24.03 |
| 4,881,184 | 11/1989 | Abegg, III et al. | 73/116 |

FOREIGN PATENT DOCUMENTS 1344617  1/1974  United Kingdom ............... 415/118

Primary Examiner—Robert Raevis
Attorney, Agent, or Firm—Peter R. Ruzek

[57] ABSTRACT

A turbine engine debris ingestion monitor has an acoustic emission sensor 18, 18a mounted on a surface 14, 14a disposed in an air flow stream of a turbine engine 12. The sensor converts acoustic emissions 16, generated by particles of debris 10 impacting on the surface, into an electrical signal. A counting circuit 22 (FIG. 2) processes the signal resulting in an output, indicative of the level of debris ingested into the engine, which is recorded in the aircraft's flight data recording system 110.

8 Claims, 3 Drawing Sheets

TURBINE ENGINE DEBRIS INGESTION MONITOR

DESCRIPTION

1. Technical Field

This invention relates to turbine engine monitors, and more particularly to turbine engine debris ingestion monitors.

2. Background Art

Turbine engine monitors are employed to evaluate the performance of a gas turbine engine during operation. The performance degradation of the engine is measured by operating efficiency. The erosion of blades, vanes, seals and other engine parts is a key factor in determining operating efficiency. Premature erosion of the engine parts is attributed to ingestion of sand, dirt, and other debris during ground operations of the airplane. Ground operations comprises taxing, take-off roll and landing roll-out. The engines mounted under the wings of an airplane are particularly susceptible to runway dirt ingestion.

Monitoring the level of debris ingested into a gas turbine engine during ground testing is known in the art. A probe is located in the air flow stream to divert a sample of the stream to a particulate filter. The debris is collected in the particulate filter during the ground testing and then removed to estimate the amount of debris ingested. However, particulate filters have not been employed in flight operations.

DISCLOSURE OF INVENTION

Objects of the present invention include provision of a turbine engine debris ingestion monitor, which monitors the level of debris ingested into a turbine engine during both flight and ground operations.

In accordance with the present invention, a particle of debris entrained in the air flow stream of a turbine engine impacts a surface of a turbine engine debris ingestion monitor, inducing a plurality of stress waves which are converted by a sensor disposed at the surface into an electrical signal that is presented to a counting circuit to provide an electrical output indicative of the level of debris ingested into the engine.

The present invention provides a continuous record of the debris ingested into the engine. The level of debris ingested during take-off roll, taxing, landing roll-out, and flight is useful in monitoring the operating efficiency of the engine. Operating procedures can be modified to minimize the level of debris ingested into the engine, thereby reducing erosion of the engine parts. Further, engine hardware design can be altered to reduce the propensity for ingesting the debris during the various stages of aircraft operation. The engine maintenance schedule can be adjusted to accommodate the actual degradation in engine efficiency as a result of debris ingestion. Further, the present invention may be used in conjunction with the flight data recording system already existing in the aircraft which records engine statistics in real-time. The present invention can be retrofitted to existing aircraft without any major alterations to the aircraft. Thus, the present invention leads to an overall improvement in monitoring turbine engine efficiency, and moreover to a safer and more reliable aircraft.

The foregoing and other objects, features and advantages of the present invention will become more apparent in light of the following detailed description of an embodiment of the invention, as shown in the accompanying drawing.

Figure 2:
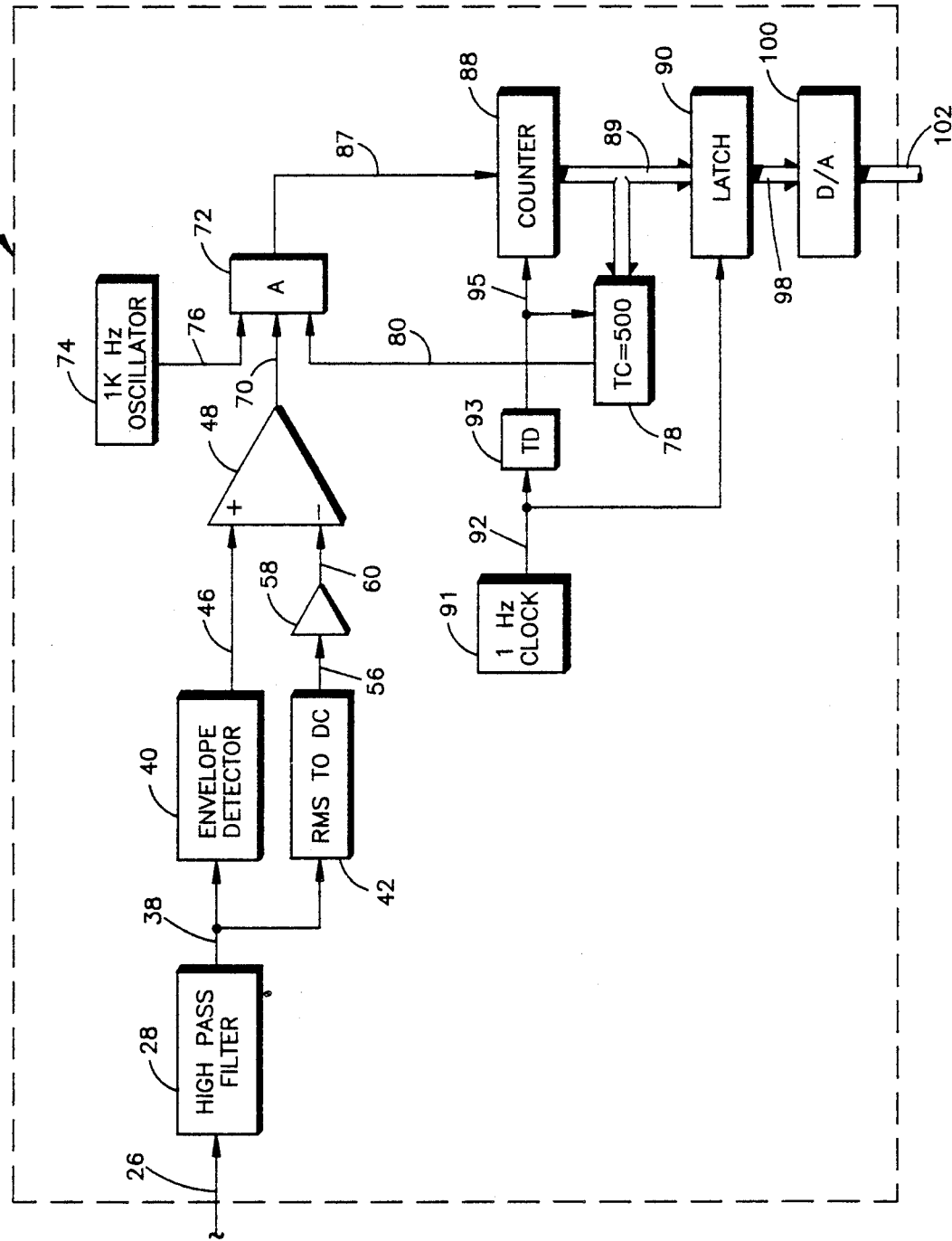
FIG. 2 is a schematic block diagram of a counting circuit.

FIG. a waveform chart illustrating waveforms in principal portions of the counting circuit in FIG. 2.

BEST MODE FOR CARRYING OUT THE INVENTION

Figure 1:
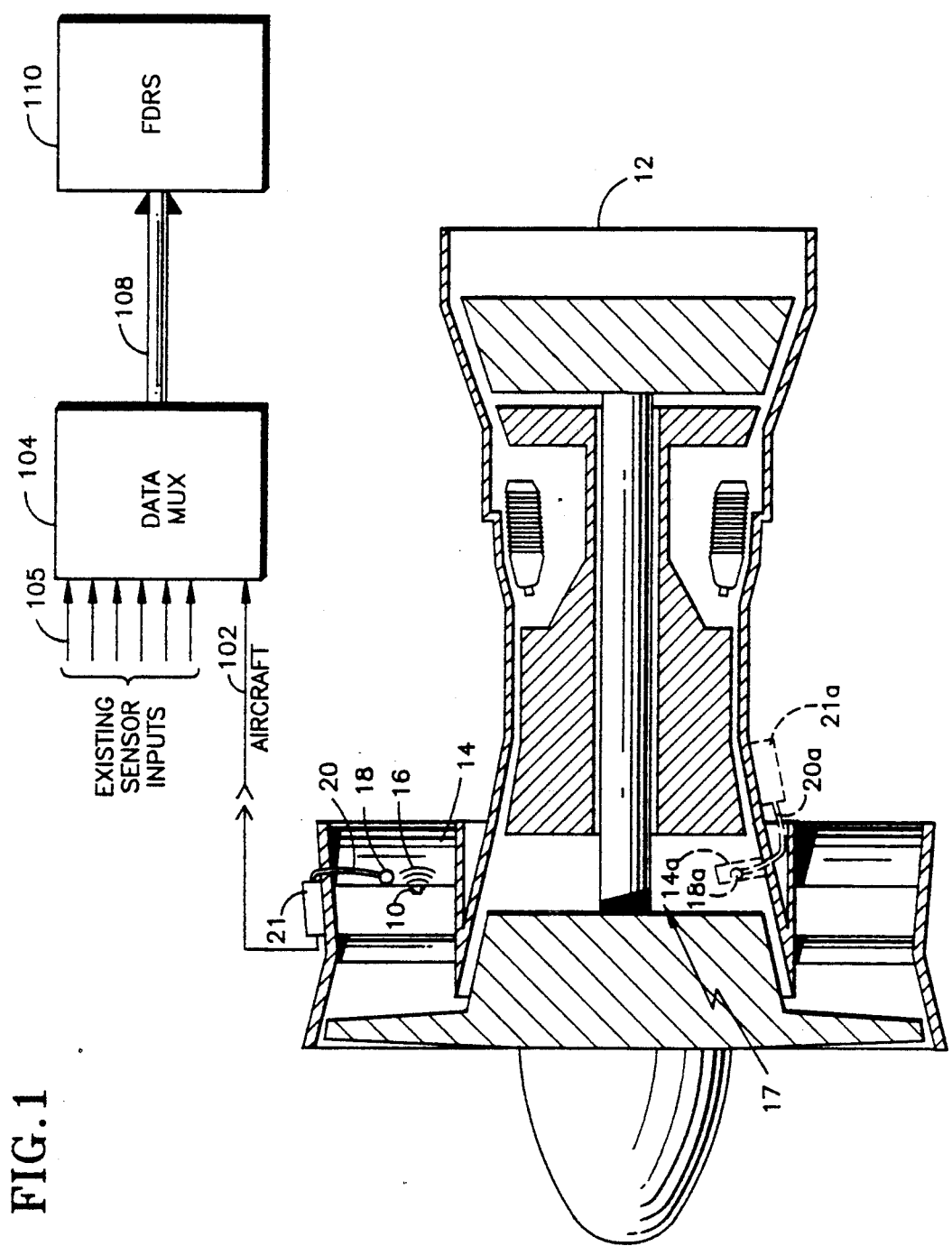
FIG. 1 is a simplified partially block diagram of an embodiment of a turbine engine debris ingestion monitor according to the present invention.

Referring now to FIG. 1, in an embodiment of the present invention, a particle of debris 10 is ingested into the air flow stream of a gas turbine engine 12. The debris impacts, at velocities in the range of 200 ft./sec. to 600 ft./sec., a sensing surface 14 disposed in the air flow stream. The energy transferred by the region underlying the impacted surface is essentially a delta function, thus resulting in a plurality of stress waves 16 having a broad frequency content. The low frequency energy is manifested as structural vibrations. Detection of debris impacting in the low frequency range is not feasible due to the large amount of normal engine vibrations in this range. The high frequency energy (frequencies above 100 kHz) from the stress waves 16 is commonly known as acoustic emission.

The stress waves generated by normal engine operations fall off rapidly at frequencies above 10 kHz and are relatively low above 100 kHz. The debris generated stress waves are generally in the 400 kHz to 600 kHz range. Thus, at high frequencies, the stress waves generated by debris impacting are sufficiently greater than the stress waves generated by normal engine operations.

The sensing surface may be a fan strut 14 (generally utilized in retrofit applications), or other engine components located in the air flow stream that are struck by debris. Further, the sensing surface may be an element 14a, shown by a dashed line, disposed in the air flow stream downstream of the low compressor exit 17. The debris carried beyond the low compressor exit impacts on the vanes and seals of the engine, causing excessive degradation of these components.

Although the front surface of an acoustic emission sensor 18, 18a may be employed as the sensing surface, the useful life on the sensor will be greatly reduced by the debris striking the sensor. Further, it is intended that a larger surface area be employed to detect a larger sample of the total debris ingested. The acoustic emissions transferred through the region underlying the impacted surface are generally detectable if such impacts take place within eight to ten inches of the sensor. This of course will vary depending on the ability of the underlying region material to be permeated by acoustic emissions. Also a surface other than the surface of the sensor protects the sensor from direct impacts, thereby increasing its useful life.

The sensor 18, 18a is mounted on the sensing surface 14 or the element 14a to detect stress waves (or so called acoustic emissions) in the region underlying the surface. The sensor is advantageously retained on the surface with epoxy. However, other methods of retaining the sensor may be employed, providing that the acoustic emissions are not suppressed by the method employed. The sensor is a piezoelectric sensor of a type known in the art, which converts acoustic emission into an electrical signal.

The electrical output of the sensor is supplied through a coaxial cable 20, 20a to electronic circuitry housed in a metal enclosure 21, 21a suitable for employment on the engine. This circuitry includes a mounting circuit 22 (FIG. 2) which may be mounted with a power supply on a circuit board (not shown). The enclosure should be mounted on the engine in close proximity to the sensor to minimize the length of the coaxial cable in order to maintain the integrity of the signal. The electronic noise generated by the engine tends to degrade the signal over increased distances.

Referring now to FIG. 2, the counting circuit 22 receives the signal output of the sensor, which is applied by a line 26 to a band pass filter 28. The filter is an active two stage, four pole frequency band pass filter. The frequency band that is passed by the filter is from 400 kHz to 1 MHz. Thus, the high stress waves generated by normal engine operations (generally below 100 kHz) are filtered out. The filter has a gain of thirty three, thereby increasing the sensor output signal (generally in the 100 to 300 mv. peak-to-peak range for the high frequencies) to a signal in the three to ten volt peak-to-peak range.

Figure 3:
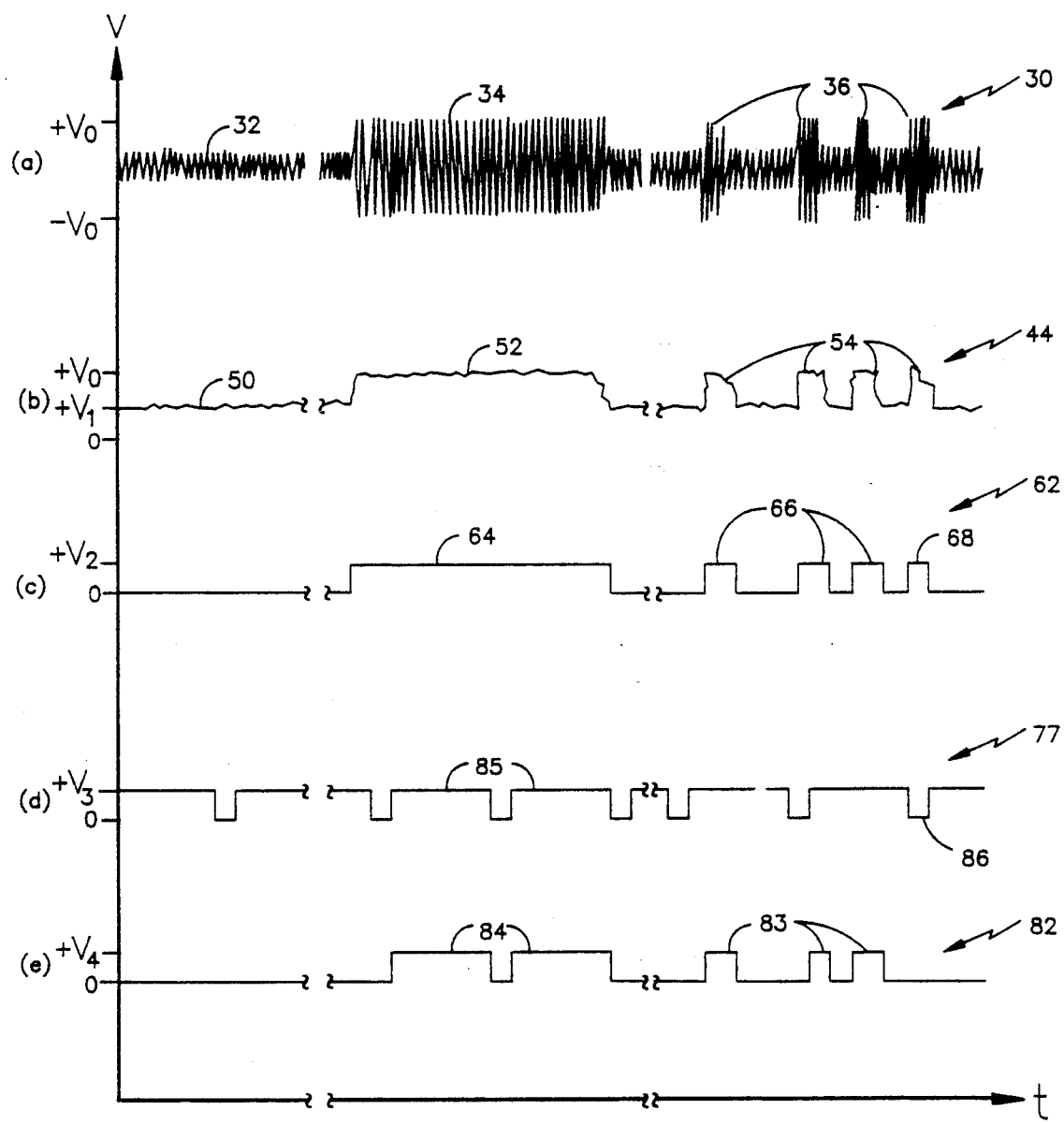

The filtered signal has a waveform 30 (FIG. 3, illustration (a)) of an bi-polar amplified high frequency (generally in the 400 kHz to 600 kHz range) portion of the sensor output signal. During a period when debris is not impacting on the sensing surface, the filtered signal is a relatively low level continuous bi-polar signal 32 indicative of the residual stress waves generated by normal engine operations. However, when many particles of debris impact the surface, each immediately following the other, the filtered signal is a higher level continuous bi-polar signal 34, until such time that the impacts are sufficiently separated to allow the stress waves to return to the level of no debris impacts. When the particle impacts are sufficiently separated in time, the filtered signal is a plurality of higher level bi-polar pulses 36. The level of the filtered signal produced by an impact is an indication of the velocity and mass of the particle (i.e. the force with which the particle impacts the surface).

The output of the filter 28 is connected by a line 38 to the inputs of both an envelope detector 40 and a RMS to DC converter 42. The envelope detector produces a waveform 44 (FIG. 3, illustration (b)) which follows the positive peaks of the filtered signal (commonly referred to as a rectified envelope). The envelope is produced by integrating the absolute value function of the filtered signal. The output of the envelope detector is connected by a line 46 to an input of a comparator 48.

Thus, during the period when debris is not impacting on the surface, the envelope is a continuous DC level 50 (FIG. 3, (b)), corresponding to the positive peaks of the filtered signal for the same time period. When particles impact, each immediately following the other, the envelope is a pulse 52 of a duration corresponding to the higher level continuous bi-polar signal portion 34 (FIG. 3, (a)) of the filtered signal. When the particle impacts are sufficiently separated in time, the envelope is a plurality of DC pulses 54 (FIG. 3, (b)) corresponding to the bi-polar pulses 36 (FIG. 3, (a)) of the filtered signal.

The RMS to DC converter 42 provides an RMS signal on a line 56 to the input of a voltage amplifier 58. The RMS signal is a continuous DC level representing the residual engine generated stress waves. The level of the residual stress waves will vary with engine speed resulting in a corresponding change in the DC level of the RMS signal.

The voltage amplifier 58 amplifies the RMS signal to produce a threshold voltage signal. The amplifier output is connected by a line 60 to another input of the comparator 48. The threshold voltage level is greater than the voltage level 50 (FIG. 3, (b)) of the envelope when debris is not impacting on the surface. The threshold voltage is employed by the comparator to detect the DC pulses 52, 54 on the output of the envelope detector. The amplifier is biased to maintain a minimum threshold voltage in order to assure that the comparator is not producing pulses when the engine is not running.

The threshold signal is compared to the envelope signal by the comparator. The comparator produces a DC output when the voltage level of the envelope signal exceeds the voltage level of the threshold signal. Thus, the output signal of the comparator is a waveform 62 (FIG. 3, illustration (c)) of pulses 64, 66, 68 corresponding to the pulses 52, 54 (FIG. 3, (b)) of the envelope wave form in excess of the threshold voltage.

Generally and hereinafter, a voltage above a logic threshold is referred to as a logic HIGH and a voltage below the logic threshold is referred to as a logic LOW. The output of the comparator is connected by a line 70 to an input of an AND gate 72. An output of a 1 kHz oscillator 74 is connected by a line 76 to another input of the AND gate. The output of the oscillator is a waveform 77 (FIG. 3, illustration (d)) of a 1 kHz gate signal, having a plurality of gate pulses with a 90% duty cycle for reducing the number of comparator output pulses that are not included in the output of the AND gate 72 (as will be described hereinafter). The 1 kHz frequency may be altered, however, it is preferred that a frequency greater than 500 Hz be employed, due to the 500 particles per second terminal count (as will also be described hereinafter). An output of a terminal counter 78 is connected by a line 80 to a third input of the AND gate 72. The terminal counter output is HIGH unless more than 500 pulses per second are produced on the output of the AND gate 72 (is also described hereinafter). Whenever the three inputs of the AND gate 72 are HIGH, the output of the AND gate 72 will also be HIGH, otherwise the output of the AND gate 72 is LOW. The output of the AND gate 72 is a waveform 82 (FIG. 3, illustration (e)) having a plurality of DC pulses 83, 84 indicative of the level of debris impacting on the sensing member.

The longer duration pulse 64 (FIG. 3, (c)) on the output of the comparator (produced during a period wherein particles impact the surface, each immediately following the other), and two of the pulses 85 (FIG. 3, (d)) from the 1 kHz oscillator occurring during the same period, are combined in the AND gate 72 to produce two pulses 84 (FIG. 3, (e)) on the output of the AND gate 72 (assuming that the terminal count output is HIGH). The number of debris impacts that produced the longer duration pulse is unknown. The 1 kHz signal provides a means for estimating the number, by producing more than a single pulse on the output of the AND gate during this period. The longer the duration of the pulse 64 (FIG. 3, (c)), the greater the number of cycles from the oscillator that will also occur resulting in more pulses 84 (FIG. 3, (e)) generated during the period.

The pulse 68 (FIG. 3, (c)) from the output of the comparator represents a particle impacting which coincides with a LOW cycle 86 (FIG. 3, (d)) of the 1 kHz signal. This comparator output pulse 68 (FIG. 3, (c)) is not included in the output waveform 82 (FIG. 3, (e)) of the AND gate 72. The information gained during periods of debris impacts immediately following each other is perceived to be of greater value than the information lost during the LOW cycles of the 1 kHz signal.

The output of the AND gate is connected by a line 87 to a counter 88. The count is indicative of the level of debris ingested into the engine. The counter is incremented by one for each pulse received during a specified time frame. An output of the counter is connected by a line 89 to both an input of a latch 90 and an input on the terminal counter 78.

A 1 Hz clock 91 produces a series of clock pulses which are fed through a line 92 to both an input on a time delay circuit 93 and another input of the latch 90. The time delay output on a line 95 assures that the counter output is latched before the counter is reset (described hereinafter). The delayed clock pulses (i.e. the time delay output) reset the counter at one second intervals. Therefore, the information provided by the counting circuit 22 will be debris impacts per second. Although the clock is described as setting the time interval to impacts per second, other time intervals may be employed, such as impacts per minute.

The time delay output is also connected by the line 95 to another input of the terminal counter 78 which limits the maximum count to 500, during the one second interval. The output of the terminal counter remains HIGH unless the count (i.e. the counter output) reaches 500, at which point the output is LOW. When the output of the terminal counter is LOW the output of the AND gate 72 will also be LOW, regardless of the output state of the comparator or the oscillator. The clock resets the terminal counter at one second intervals returning the output of the terminal counter to a HIGH, thus allowing the AND gate to resume presenting pulses to the counter.

The 500 debris impacts per second limit is a level of debris ingestion at which the rate of engine degradation is beyond generally accepted engine tolerance. The count is only a sample of the debris ingested into the air flow steam, from which the overall ingestion level may be interpolated. The distribution of debris ingested into the air flow stream is believed to be uniform; however, additional sensors may be employed for additional sampling, if desired. The terminal count may be set at limits other than the 500 particles of debris per second described herein.

The output count is latched by a clock pulse and held by the latch for a one second interval. The counter 88 is not reset until a fixed time period after the count is latched. The fixed time period is the delay time of the time delay circuit, thus assuring that the count for a time interval is latched before the counter is reset and begins counting for the next time interval.

The latch output is connected by a line 98 to the input of a digital-to-analog converter 100, hereinafter referred to as "D/A", which converts the count into an analog signal. This converted analog signal is indicative of the level of debris ingested into the engine. During the next second, the output of the counter, which was reset in the prior one second interval, is latched and converted by the D/A. This process is repeated at one second intervals. The output of the D/A on a line 102 is the output of the counting circuit.

The counting circuit output is connected by the line 102 (FIG. 1) to a aircraft's data multiplexer 104 and multiplexed with other sensor signals 105. The multiplexer output is connected by a line 108 to an aircraft's flight data recording system 110, hereinafter referred to as "FDRS". The FDRS records various engine statistics, which are periodically evaluated in order to monitor engine efficiency. The signal indicative of the level of debris ingested into the engine (i.e. counting circuit output) may also be recorded in real-time by the FDRS. Further, the signal may be employed as a display or warning signal of debris ingestion level.

The FDRS 110 is described utilizing (through the data multiplexer) the output of the counting circuit, however, other devices capable of utilizing the output may be employed. A computer or a digital version of the FDRS may eliminate the need for the circuitry following the output of the AND gate 72 (FIG. 2), without departing from the scope of the invention.

It suffices for the broadest scope of the present invention that the debris ingested into the engine air flow stream impacts a surface generating an acoustic emission which is detected by the sensor and converted into an electrical signal indicative of the debris impacts. Similarly, although the invention has been described with respect to an exemplary embodiment thereof, it should be understood by those skilled in the art that the foregoing and various other changes, omissions and additions in the form and detail thereof may be made therein and thereto, without departing from the spirit and scope of the invention.

We claim:

1. Apparatus for detecting debris ingested into an air flow stream of a turbine engine during the operation thereof, comprising:

sensor means having a sensor surface disposed in the air flow stream to be struck by the debris for producing a plurality of stress waves indicative of both impact stressed resulting from debris impacts and background stresses resulting from the operation of the engine, and means for converting said stress waves into an analog electrical signal having a plurality of bipolar pulses each indicative of the debris striking said surface;

bandpass filter means receiving said electrical signal and issuing a filtered electrical signal devoid of at least a great proportion of those frequency components of said electrical signal at which the effect of said impact stresses on the amplitude of said electrical signal is indistinguishable from that of said background stresses; and signal processing means, responsive to said filtered electrical signal for providing an output signal having a plurality of output pulses derived from said bipolar pulses and indicative of a level of debris ingested into the engine.

2. Apparatus according to claim 1 wherein said surface comprises a turbine engine component.

3. Apparatus according to claim 2 wherein said surface comprises a fan strut.

4. Apparatus according to claim 1 wherein said signal processing means comprises:

envelope detector means, responsive to said filtered electrical signal, for providing an envelope signal having a plurality of envelope pulses each indicative of each of said bipolar pulses;

threshold means, responsive to said filtered electrical signal, for providing a threshold signal indicative of stress waves induced by both debris impacts and engine operations;

comparator means, responsive to both envelope signal and said threshold signal, for providing a compared signal having a plurality of compared pluses each indicative of each of said envelope pulses in excess of said threshold signal; and gate means for providing a periodic gate signal having a plurality of gate pulses, and means for gating said compared signal occurring coincidentally in time with each of said gate pulses for providing said output pulses.

5. Apparatus according to claim 1 further comprising count means, responsive to said output pulses, for providing a cumulative count of said pulses within a fixed time period, said cumulative count having a digital output.

6. Apparatus according to claim 5 further comprising conversion means, responsive to said digital output, for converting said digital output into an analog output; and record means, responsive to said analog output, for recording said analog output.

7. Apparatus according to claim 5 further comprising record means, responsive to said digital output, for recording said digital output.

8. Apparatus according to claim 1 further comprising record means, responsive to said output pulses, for recording said output pulses.

* * * * *

UNITED STATES PATENT AND TRADEMARK OFFICE
CERTIFICATE OF CORRECTION

PATENT NO. : 5,070,722

DATED : December 10, 1992

INVENTOR(S) :
Michael W. Ritter et al

It is certified that error appears in the above-identified patent and that said Letters Patent is hereby corrected as shown below:

Column 7, claim 4, line 3 "pluses" should be ---pulses---.

Signed and Sealed this

Nineteenth Day of October, 1993

Attest:

BRUCE LEHMAN

Attesting Officer     Commissioner of Patents and Trademarks